(12) United States Patent
Hulteen et al.

(10) Patent No.: US 7,888,129 B2
(45) Date of Patent: Feb. 15, 2011

(54) SURFACE-ENHANCED SPECTROSCOPIC METHOD, FLEXIBLE STRUCTURED SUBSTRATE, AND METHOD OF MAKING THE SAME

(75) Inventors: John C. Hulteen, Afton, MN (US); Lisa A. Dick, Afton, MN (US); Haiyan Zhang, Woodbury, MN (US); William L. Stebbings, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 12/621,673

(22) Filed: Nov. 19, 2009

(65) Prior Publication Data
US 2010/0062226 A1     Mar. 11, 2010

Related U.S. Application Data

(62) Division of application No. 11/181,151, filed on Jul. 14, 2005, now Pat. No. 7,651,863.

(51) Int. Cl.
*G01N 21/03* (2006.01)
*B05D 5/00* (2006.01)
*B05D 3/00* (2006.01)

(52) U.S. Cl. ................. 436/165; 427/256; 427/275; 977/724

(58) Field of Classification Search ................ 436/165
See application file for complete search history.

(56) References Cited

U.S. PATENT DOCUMENTS

| | | |
|---|---|---|
| 3,927,692 A | 12/1975 | Wenrich |
| 4,674,878 A | 6/1987 | Vo Dinh |
| 4,781,952 A | 11/1988 | Coscia et al. |
| 5,017,007 A | 5/1991 | Milne et al. |
| 5,025,052 A | 6/1991 | Crater et al. |
| 5,039,561 A | 8/1991 | Debe |
| 5,099,026 A | 3/1992 | Crater et al. |
| 5,244,951 A | 9/1993 | Gardiner |
| 5,255,067 A | 10/1993 | Carrabba et al. |
| 5,300,263 A | 4/1994 | Hoopman et al. |
| 5,300,357 A | 4/1994 | Gardiner |
| 5,380,778 A | 1/1995 | Buckanin |
| 5,451,622 A | 9/1995 | Boardman et al. |
| 5,521,030 A | 5/1996 | McGrew |

(Continued)

FOREIGN PATENT DOCUMENTS

| | | |
|---|---|---|
| CN | 1445385 A | 10/2003 |
| DE | A9941048 AI | 3/2001 |
| DE | 10064520 A1 | 7/2002 |
| WO | WO 00/73082 A2 | 2/2000 |
| WO | WO 01/88575 A2 | 12/2000 |
| WO | WO 91/02228 | 2/2001 |
| WO | WO 2006/048660 | 5/2006 |

OTHER PUBLICATIONS

"Aluminum Finishes Process Manual", Reynolds Metal Company, Richmond, Virginia, 1973, pp. 62-113.

Bonn et al., "Theory of sum-frequency generation spectroscopy of absorbed molecules using the density matrix method—broadband vibrational sum-frequency generation and applications", 2005, J. Phys.: Condens. Matter, vol. 17, pp. S201-5220.

(Continued)

*Primary Examiner*—Sam P Siefke
*Assistant Examiner*—Bryan T Kilpatrick
(74) *Attorney, Agent, or Firm*—Kenneth B. Wood

(57) ABSTRACT

A method of obtaining a surface-enhanced optical property of an analyte using a flexible structured substrate having a metal layer conformably disposed on nanostructure, a flexible structured substrate, and a method of making the same.

17 Claims, 3 Drawing Sheets

U.S. PATENT DOCUMENTS

| | | | |
|---|---|---|---|
| 5,659,408 | A | 8/1997 | Wenyon |
| 5,674,592 | A | 10/1997 | Clark et al. |
| 5,751,415 | A | 5/1998 | Smith et al. |
| 5,792,411 | A | 8/1998 | Morris et al. |
| 5,804,625 | A | 9/1998 | Temperante et al. |
| 5,882,762 | A | 3/1999 | Goeman |
| 5,930,040 | A | 7/1999 | Janovec et al. |
| 6,040,191 | A | 3/2000 | Grow |
| 6,076,248 | A | 6/2000 | Hoopman et al. |
| 6,127,485 | A | 10/2000 | Klun et al. |
| 6,174,677 | B1 | 1/2001 | Vo Dinh |
| 6,174,964 | B1 | 1/2001 | Jariwala et al. |
| 6,190,594 | B1 | 2/2001 | Gorman et al. |
| 6,262,180 | B1 | 7/2001 | Klun et al. |
| 6,284,843 | B1 | 9/2001 | Jariwala et al. |
| 6,288,157 | B1 | 9/2001 | Jariwala et al. |
| 6,368,534 | B1 | 4/2002 | Nakamura et al. |
| 6,376,065 | B1 | 4/2002 | Korba et al. |
| 6,380,289 | B1 | 4/2002 | Thompson, Jr. et al. |
| 6,391,807 | B1 | 5/2002 | Jariwala et al. |
| 6,489,377 | B1 | 12/2002 | Bicer et al. |
| 6,514,597 | B1 | 2/2003 | Strobel et al. |
| 6,527,991 | B1 | 3/2003 | Bakker et al. |
| 6,576,887 | B2 | 6/2003 | Whitney et al. |
| 6,586,522 | B1 | 7/2003 | Jariwala et al. |
| 6,622,599 | B1 | 9/2003 | Ben-Menachem et al. |
| 6,641,767 | B2 | 11/2003 | Zhang et al. |
| 6,646,019 | B2 | 11/2003 | Perez et al. |
| 6,649,249 | B1 | 11/2003 | Engle et al. |
| 6,737,160 | B1 | 5/2004 | Full et al. |
| 6,823,653 | B1 | 11/2004 | Stark et al. |
| 6,824,378 | B2 | 11/2004 | King et al. |
| 6,877,216 | B2 | 4/2005 | Fukuda et al. |
| 6,985,818 | B1 | 1/2006 | Samuels |
| 7,105,809 | B2 * | 9/2006 | Wood et al. ............ 250/288 |
| 2001/0051264 | A1 * | 12/2001 | Mazurek et al. ......... 428/343 |
| 2002/0084553 | A1 | 7/2002 | Nun et al. |
| 2003/0059954 | A1 | 3/2003 | Vikholm et al. |
| 2003/0068481 | A1 | 4/2003 | Kody et al. |
| 2003/0155246 | A1 | 8/2003 | Schimmel et al. |
| 2003/0157347 | A1 | 8/2003 | Zhang et al. |
| 2003/0187170 | A1 | 10/2003 | Burmeister |
| 2004/0043146 | A1 | 3/2004 | Pellerite et al. |
| 2004/0094705 | A1 * | 5/2004 | Wood et al. ............ 250/288 |

OTHER PUBLICATIONS

Chou et al., "Nanoimprint Lithography", Nov./Dec. 1996, J. Vac. Sci. Technol. B., vol. 14, No. 6, pp. 4129-4133.
Chou et al., "Imprint Lithography with 25-Nanometer Resolution", Science, Apr. 5, 1996, vol. 272, pp. 85-87.
Chou et al., "Imprint of sub-25 nm vias and trenches in polymers", Appl Phys. Lett., Nov. 20, 1995, vol. 67, No. 21, pp. 3114-3116.
Chou et al., "Sub-10 nm imprint lithography and applications", Nov./Dec. 1997, J. Vac. Sci. Technol. B., vol. 15, No. 6, pp. 2897-2904.
Dick, et al., "Metal Film over Nanosphere (MFON) Electrodes for Surface-Enhanced Raman Spectroscopy (SERS): Improvements in Surface Nanostructure Stability and Suppression of Irreversible Loss", 2002, Published on the Web Dec. 27, 2001 J. Phys. Chem.B., vol. 106, No. 4, pp. 853-860.
Foss et al., "Optical Properties of Composite Membranes Containing Arrays of Nanoscopic Gold Cylinders", 1992, J. Phys. Chem., vol. 96, No. 19, pp. 7497-7499.
Foss et al., "Optical Properties of Composite Membranes Containing Arrays of Nanoscopic Gold Cylinders", J. Phys. Chem. 1992, vol. 96, pp. 7497-7499.
Frey et al., "Microfabrication Using Patterned Topography and Self-Assembled Monolayers", U.S. Appl. No. 11/003,233, filed Dec. 3, 2004.
Fleischmann et al., "Raman Spectra of Pyridine Absorbed at a Silver Electrode", May 15, 1974, Chemical Physics Letters, vol. 26, No. 2, pp. 163-166.
Goudonnet et al., "Surface-Enhanced Raman Scattering on Silver-Coated Teflon Sphere Substrates", Oct. 15, 1982, Chemical Physics Letters, vol. 92, No. 2, pp. 197-201.
Handbook of Vibrational Spectroscopy, J. M. Chalmers, and P.R. Griffiths (Editors), John Wiley & Sons Ltd. Chichester, England, 2002, pp. 1-16.
Hoyer, "Semiconductor Nanotube Formation by a Two-Step Template Process", Advanced Materials, 1996, vol. 8, No. 10, pp. 857-859.
Haisma et al., "Mold-assisted nanolithography: A process for reliable pattern replication", Nov./Dec. 1996, J. Vac. Sci. Technol. B., vol. 14, No. 6, pp. 4124-4128.
Hulteen et al., "Nanosphere lithography: A materials general fabrication process for periodic particle array surfaces", May/Jun. 1995, J. Vac. Sci. Technol. A., vol. 13, No. 3, pp. 1553-1558.
Jung, „Manufacturing of Nanostructured Substrate, Found on website: http://plaza.snu.ac.kr/~jinklee/first.htm—Publications—Local Conference—Publication.
Kahl et al., "Periodically structured metallic substrates for SERS", 1998, Sensors and Actuators B, vol. 51, pp. 285-291.
Lu et al., „High-Density Silver Nanoparticle Film with Temperature-Controllable Interparticle Spacing for a Tunable Surface Enhanced Raman Scattering Substrate, Nano Letters, Jan. 2005, vol. 5, No. 1, pp. 5-9.
Masuda et al., "Fabrication of Pt microporous electrodes from anodic porous alumina and immobilization of GOD into their micropores", Journal of Electroanalytical Chemistry, 1994, vol. 368, pp. 333-336.
Martin, "Nanomaterials: A Membrane-Based Synthetic Approach", Science, Dec. 23, 1994, vol. 266, pp. 1961-1966.
Nie et al., "Probing Single Molecules and Single Nanoparticles by Surface-Enhanced Raman Scattering", Feb. 21, 1997, Science, vol. 275, No. 21, pp. 1102-1106.
Proceedings of Symposium "Defect Structure Morphology and Properties of Deposits—Surface Morpholgy of Electrodeposits", Rosemont, Illinois, Oct. 4-6, 1994, The Minerals, Metals and Materials Society, pp. 114-167.
Pinner, "Copper and Alloy Plating", Copper Development Association, London, C.D.A. Publication No. 62, 1962, Second Ed., 1964, pp. 3, 26-41, 72-77.
Schatz et al., "Electromagnetic Mechanism of Surface-enhanced Spectroscopy", from.
Szabo et al. „Surface-Enchanced Raman Scattering from an Etched Polymer Substrate, Anal. Chem. 1997, 69, p. 2418-2425.
Schafer-Peltier, "Toward a Glucose Biosensor Based on Surface-Enhanced Raman Scattering", 2003, J. Am Chem. Soc., vol. 125, pp. 588-593.
Vo-Dinh et al., "Recent advances in surface-enhanced Raman spectrometry for chemical analysis", 1988, Spectrochimica Acta, vol. 43B, Nos. 4/5, pp. 605-615.
Viets et al., "8. Fiber-optic SERS sensors", [retrieved from the internet on Jun. 8, 2005], The Internet Journal of Vibrational Spectroscopy, vol. 4, Edition 2, <http://www.ivjs.com/volume4/edition2/section7.html>, 13 pages.
Yao et al., "A complimentary study of surface-enhanced Raman scattering and metal nanrod arrays", 2000, Pure Appl. Chem. vol. 72, No. 1, pp. 221-228.
Young et al., "Surface enhanced Raman spectroscopy with a laser pointer light source and miniature spectrometer", 2004, Can. J. Chem., vol. 82, pp. 1435-1441.
Zhang, "Tool and Method of Making and Using the Same", U.S. Appl. No. 11/181,150, filed Jul. 14, 2005.
Zhang et al., "Nanostructured Article and Method of Making the Same", U.S. Appl. No. 11/181,153, filed Jul. 14, 2005.
Zhang et al., "Rapid Detection of an Anthrax Biomarker by Surface-Enhanced Raman Spectroscopy", Published on Web Mar. 8, 2005, J. Am. Chem. Soc., vol. 127, No. 12, pp. 4484-4489.

* cited by examiner

SURFACE-ENHANCED SPECTROSCOPIC METHOD, FLEXIBLE STRUCTURED SUBSTRATE, AND METHOD OF MAKING THE SAME

CROSS REFERENCE TO RELATED APPLICATIONS

This application is a divisional of U.S. patent application Ser. No. 11/181,151, filed Jul. 14, 2005 now U.S. Pat. No. 7,651,863, the disclosure of which is herein incorporated by reference.

BACKGROUND

Generally, surface-enhanced spectroscopy involves spectroscopic analysis of an analyte that is in close proximity to a metallic surface having sub-micron sized topographical features. Under these conditions, the spectroscopic signal may be increased by spatially confining the analyte within range of the electromagnetic fields generated upon excitation of the localized surface plasmon resonance of the metal surface at the topographical features.

A variety of spectroscopic analysis techniques have been shown to benefit from this type of surface effect including: surface-enhanced Raman spectroscopy (SERS), surface plasmon resonance spectroscopy, surface-enhanced infrared spectroscopy, and surface-enhanced sum frequency generation spectroscopy.

Typically, such techniques are conducted by bringing a substance to be analyzed (e.g., a gas, liquid, or solid) in close proximity to the metal layer that is supported on a relatively small area (e.g., 1 cm by 1 cm) substrate. Through this technique the signal of an analyte may be increased in intensity by up to 8 orders of magnitude (or more) depending on conditions, and in some cases may even be sensitive enough to detect even individual molecules.

SUMMARY

In one aspect, the present invention provides a method of analyzing a substance comprising:
(a) providing a flexible structured substrate comprising:
(i) a monolithic polymeric film comprising:
a base having first and second opposed major surfaces, wherein at least a portion of the first major surface is at least partially defined by nanostructure; and
(ii) a metal layer conformably disposed on at least a portion of the nanostructure;
(b) providing an analyte in close proximity to at least a portion of the metal layer; and
(c) observing a surface-enhanced optical property of the analyte.

In one embodiment, the method can be advantageously practiced with an inventive structured substrate.

Accordingly, in another aspect, the present invention provides a structured substrate comprising:
(a) a monolithic polymeric film comprising:
a base having first and second opposed major surfaces, wherein at least a portion of the first major surface is at least partially defined by:
a patterned microstructure outwardly extending from the base; and
nanostructure having an average height of at least 100 and less than 200 nanometers, wherein the nanostructure is at least partially encompassed within, or overlaps, the patterned microstructure; and (b) a metal layer conformably disposed on at least a portion of the nanostructure, wherein the structured substrate is flexible.

In another aspect, structured substrates according to the present invention may be manufactured by a process that is reproducible on a nanometer-scale. In one embodiment, a roll of structured substrate according to the present invention may be cut into many pieces (e.g., diced), for example, for use as SERS substrates. Accordingly, when making SERS measurements, the pieces typically exhibit little or no variation between SERS signals obtained for the same level of analyte.

Accordingly, in yet another aspect, the present invention provides a method of manufacturing a structured substrate comprising:
providing a tool having a continuous surface with a first patterned microstructure thereon;
continuously forming a monolithic polymeric film comprising a base having first and second opposed major surfaces, wherein at least a portion of the first major surface comprises a second microstructure having a first height and outwardly extending from the base, wherein the second microstructure is substantially complementary to the first microstructure; and
forming nanostructure having an average height of at least 100 and less than 200 nanometers, and wherein the nanostructure is at least partially encompassed within, or overlaps, the microstructure; and
conformably disposing a metal layer on at least a portion of the nanostructure, wherein the structured substrate is flexible.

In addition to the aforementioned reproducibility, structured substrates according to the present invention may be obtained in large quantity, and at relatively lower cost on a volume basis as compared to existing techniques.

Further, structured substrates according to the present invention typically have good stability over time.

As used herein:
"base" refers to the maximum volume portion of a film of constant thickness not including a microstructured or nanostructured pattern;
"embossed random pattern" means that over short distances the pattern is random, but includes patterns in which the entire random pattern repeats with a periodicity much greater than the distance between embossed random features;
"feature heights" are to be determined normal to the base;
"flexible", as applied to a structured substrate, means that the substrate can be manually rolled upon itself at 25° C. and with a radius of curvature of less than 1 cm;
"monolithic" means consisting of or constituting a single unit;
"raised nanofeature" refers to a protuberance having a height of at least 5 nanometers and less than 1 micrometer;
"nanostructure" refers to a plurality of raised nanofeatures at least about $1 \times 10^7$ nanofeatures per square centimeter, or a network of interconnected raised nanofeatures (e.g., raised nanofeatures connected by ridges or arches), outwardly extending from the base and having an average height of at least 5 nanometers and less than 1 micrometer; by definition nanostructure is not smooth;
"optical property" refers to ultraviolet, visible or infrared electromagnetic radiation that is absorbed by, or emitted from, an analyte;
"patterned microstructure" refers to a predetermined pattern with feature heights in a range of from 1 micrometer to 5 millimeters;
"polymeric" means comprising an organic polymer;
"thermoset" means covalently crosslinked; and "thermosettable" means covalently crosslinkable by application of heat or light.

DETAILED DESCRIPTION

Figure 1:
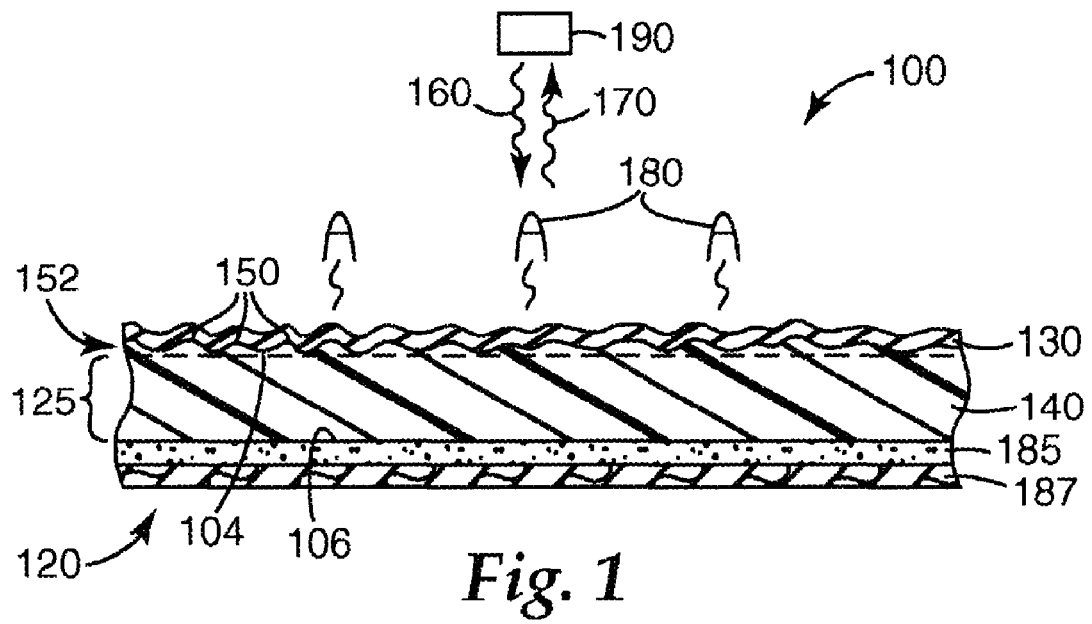
FIG. 1 is a schematic representation of an exemplary method of analyzing a substance according to the present invention.

Referring now to FIG. 1, the present invention provides a method 100 of analyzing a substance. The method utilizes a flexible structured substrate 120 that comprises a monolithic polymeric film 140. Film 140 has base 125 and first and second opposed major surfaces 104, 106, respectively. At least a portion of first major surface 104 is defined by nanostructure 152 consisting of raised nanofeatures 150. Raised nanofeatures 150 outwardly extend from base 125. Metal layer 130 is conformably disposed on at least a portion of the nanostructure 152. Analyte 180 is brought into close proximity to at least a portion of metal layer 130. A probe beam of radiation 160 is directed at analyte 180 and signal 170 containing information concerning at least one surface-enhanced optical property of analyte 180 is observed by detector 190. Structured substrate 120 may optionally have adhesive layer 185 disposed on second major surface 106. Optional release liner 187 is releasably bonded to optional adhesive layer 185.

Surface-enhanced optical properties that can be measured according to the present invention include, for example, vibrational properties which may be observed using surface-enhanced infrared absorption spectroscopy, surface-enhanced Raman emission spectroscopy (e.g., SERS) and/or surface-enhanced sum frequency generation spectroscopy, and polarization properties which may be observed using surface plasmon resonance spectroscopy.

Various spectroscopic methods for observing the foregoing properties are well known in the art and include SERS, surface plasmon resonance spectroscopy, surface-enhanced infrared spectroscopy, surface-enhanced sum frequency generation spectroscopy, and surface-enhanced hyper-Raman spectroscopy. For example, practical details concerning SERS have been reported, for example, by G. C. Schatz and R. P. Van Duyne in "Electromagnetic Mechanism of Surface-enhanced Spectroscopy" as reproduced from *Handbook of Vibrational Spectroscopy*, J. M. Chalmers and P. R. Griffiths (Editors), John Wiley & Sons Ltd.: Chichester, England©2002, pages 1-16.

Generally, the analyte must be brought into sufficiently close proximity that interactions with surface plasmons of the metal layer may occur. Typically, this is a distance of a few nanometers or less.

Methods according to the present invention have applicability to chemical and biological sensing. Examples of analytes that may be observed and/or quantitatively measured according to the present invention include pesticides, bacteria, viruses, DNA, nucleic acids, nucleic acid analogues, proteins, peptides, amino acids, enzymes, prions, antibodies, aldehydes, amines, ketones, explosive residues, drugs of abuse, therapeutic agents, metabolites and environmental pollutants. This list is not however exhaustive, as any suitable analyte may be detected.

The analyte may be obtained from a sample and the sample may be any suitable preparation in which the target analyte is likely to be found. However, conveniently the analyte may be in vapor or aerosol form, or in a fluid or solution, or transferred to a solution before applying the analyte to the flexible structured substrate, typically followed by evaporation of any solvent carrier that may be present. Thus, for example, when detecting explosives or drugs of abuse, a sample of gas, such as air or breath respectively, may be taken and any target analyte absorbed onto a suitable substrate.

Thereafter, any target analyte may be removed from the flexible structured substrate by washing with a suitable solvent, or more typically and in keeping with the advantages of the present invention the structured substrate may be simply discarded after use.

To facilitate confinement of the analyte in proximity to the metal layer, one or more optional reagents may be bound (e.g., by physical adsorption, ionic bonding, or covalent bonding) to the metal layer. Optional reagents may be selected to have a high affinity for a target analyte; for example, a receptor for a biomolecule or a cage-like structure such as a cyclodextrin for binding aromatic molecules. In one embodiment, the reagent may have a terminal ionizable or ionic group (e.g., $-OPO_3H_2$, $-O-P(O)_2(OH)^-$, $-CO_2H$, $-CO_2^-$, $-SO_3H$, $-SO_3^-$, $-NR_2$, or $-NR_3^+$ wherein R is H, or a lower alkyl group) as, for example, in the case of $HS(CH_2)_3CO_2H$.

The flexible structured substrate may have any length, width, or thickness provided that it is flexible as defined hereinabove. Flexibility of the structured substrate allows the use of manufacturing techniques that are suitable for reproducible large-scale production of structured substrates. Until now, existing methods of fabricating structured substrates have not lent themselves to reproducible large-scale production. Accordingly, the present invention makes it possible to measure surface-enhanced optical properties quantitatively and in real time.

The polymeric film may comprise one or more thermoplastic or thermoset polymeric materials, or any combination thereof. For example, the polymeric film may comprise a blend of two or more thermoplastic polymeric materials.

Useful thermoplastic polymeric materials include, for example, polyesters (e.g., polyethylene terephthalate), polyamides (e.g., nylon-6, nylon-6,6), polyolefins (e.g., polypropylene and polyethylene), ethylene-vinyl acetates (EVAs), polyurethanes, acrylics, fluoropolymers, and engineering thermoplastics (e.g., polyimides, polycarbonates and polyether ether ketones), and combinations thereof.

If used, useful thermoset polymeric materials are typically formed from thermosettable polymeric material that has been formed into a predetermined desired shape prior to curing, although this is not a requirement, for example, if the thermoset polymeric material is embossable. For example, a thermosettable polymeric material may be applied to a tool having a structured surface that is complimentary to the desired first film surface, and then subsequently cured. Useful thermosettable polymeric materials include, for example, curable silicones, natural and synthetic rubbers, curable fluoroelastomers, epoxies, melamines, polyacrylates, alkyd resins, polyurethane precursors, and combinations thereof. Thermosettable materials may include an effective amount of one or more curatives (e.g., crosslinkers, catalysts, photoinitiators). If used, the thermosettable materials may be cured (i.e., covalently crosslinked) by any suitable method such as, for example, application of heat, e-beam radiation, and/or ultraviolet radiation.

Nanostructure consists of raised nanofeatures. The raised nanofeatures extend outwardly from the base of the structured substrate may independently have any height in a range of from at least 5, 10, 20, 50 or even at least 100 nanometers up to 200, 250, 400, 500, 750 or even up to, but not including, 1000 nanometers (1 micrometer). In one embodiment, the nanostructure may have an average height, measured normal to the base, of less than 400 nanometers or less than 200 nanometers. For example, the nanostructure may have an average height, measured normal to the base, of at least 100 and less than 200 nanometers.

In some embodiments, the nanostructure may be continuous as, for example, in the case of a network of raised interconnected nanofeatures of varying height. In some embodiments, the nanostructure may be discontinuous as, for example, a plurality of discrete raised nanofeatures.

Generally, the surface effect on optical properties increases with the density of the nanostructure. Accordingly, in some embodiments, the areal density of the discrete nanofeatures on at least a portion of the base is typically at least about $1 \times 10^7$ nanofeatures/cm$^2$, for example, at least about $1 \times 10^8$, $1 \times 10^9$, $1 \times 10^{10}$, or even at least about $1 \times 10^{11}$ nanofeatures/cm$^2$; and, in some embodiments, in regions of the structured substrate having nanostructure, the projected area (along a line normal to the base) of the nanostructure onto the base may be at least 30, 40, 50, 60, 70, 80, 90 percent or more of the corresponding surface area of the base.

Raised nanofeatures may be randomly shaped or may be shaped according to a regular geometric pattern (e.g., regularly sized square pyramids). Typically, the raised nanofeatures are relatively uniformly distributed such that signals obtained in one region of raised nanofeatures are comparable to (within an order of magnitude), for example, typically substantially identical to, signals obtained from another region of nanostructure situated elsewhere on the structured substrate.

In some embodiments such as, for example, those in which the structured substrate is formed by a continuous web process such as, for example, that described hereinbelow, the variation in the nanostructure is typically minimal in cross-web and down-web directions. As a result, pieces of structured substrate of suitable size for analysis (e.g., 1 cm×1 cm) that are cut from the same continuously manufactured web will typically have comparable or substantially identical sensitivity during observation of a surface-enhanced optical property of an analyte. Similarly, a tape cut from a continuously manufactured web will typically have comparable or substantially identical sensitivity along its length during observation of a surface-enhanced optical property of an analyte.

In order to maximize signal sensitivity, the nanostructure is typically disposed as one or more continuous regions of closely packed raised features.

In some embodiments, at least a portion of the first surface of the structured substrate further is partially defined by a patterned microstructure in addition to the nanostructure. The patterned microstructure extends outwardly from the base of the structured substrate. The pattern may be random, pseudo-random, regular, or a combination thereof.

The patterned microstructure and nanostructure are typically disposed such that the nanostructure is at least partially encompassed within, or overlap, the patterned microstructure. For example, in one embodiment at least one region of the microstructure has an average width of at least 1 micrometer and encompasses at least a portion of the nanostructure.

The patterned microstructure may comprise, for example, cylindrical posts, prismatic posts, parallel ribs, intersecting ribs, and combinations thereof. In some embodiments, the ribs may form conduits that cause wicking of liquids, for example, as a sample loading mechanism.

The patterned microstructure is advantageous in that it provides a degree of protection from abrasion (e.g., during handling or winding up in roll form) to the conformably coated metal layer disposed on the nanostructure. Accordingly, the average height of the patterned microstructure is typically selected such that it is at least three times the average height of the nanostructure. For example, the average height of the patterned microstructure may be selected such that it is at least 5, 10, 25, or even at least 50 times the average height of the nanostructure. In one embodiment, average height of the microstructure is at least 10 micrometers Further, while the patterned microstructure may have some smaller scale texture, it is typically desirable that the surfaces of the patterned microstructure be at least substantially free of nanostructure as such features might give rise to surface-enhanced optical properties and would be relatively prone to damage, for example, by abrasion thereby causing variation in sensitivity of the structured substrate.

Generally, the patterned microstructure should have sufficient openings to allow at least a full width of a probe laser beam to reach the nanostructure. For example, the openings in the patterned microstructure may have minimum width of at least 20, 40, 60, 100, 150, or even 250 nanometers or more.

The metal layer is conformably disposed on at least a portion of the nanostructure, and more typically on substantially all of the nanostructure. The choice of metal typically will depend on the optical property and/or specific analyte being measured. Examples of suitable metals that are known to give surface enhancement of optical properties include alkali metals (e.g., lithium, sodium, and potassium), noble metals (i.e., silver, gold, platinum, palladium, ruthenium, and iridium) and other transition metals (e.g., copper, zinc, nickel, iron, cobalt, and rhodium), aluminum, alloys thereof, and combinations thereof.

Typically, the metal layer has a substantially uniform thickness. To obtain surface enhanced optical properties, the average thickness of the metal layer should typically be in a range of from at least 5, 10, or even 25 nanometers up to 50, 100, 200, 300, or even 500 nanometers, as long as the outermost surface of the metal layer has substantially the same texture as the underlying nanostructure (i.e., it substantially conforms to the nanostructure). While the metal layer may be continuous or discontinuous (e.g., if separated by ribs), it is typically continuous over distances of at least 100 nanometers.

While the metal layer may be disposed on the patterned microstructure in addition to the nanostructure, it is typically unnecessary, and may even be undesirable in some instances.

The structured substrate may have any suitable shape, typically as dictated by the specific choice of analytical technique and equipment. For example, the structured substrate may be in the form of a roll, sheet, or tape. In one embodiment, the structured substrate may have dimensions on the order of 1 cm×1 cm. The structured substrate may be perforated, for example, if in the form of a roll or tape to facilitate removal of small portions.

Optionally, the structured substrate may have a layer of adhesive disposed on the second major surface of the polymeric film. Suitable adhesives include, for example, pressure sensitive adhesives, and low temperature melting hot-melt adhesives. In the case of pressure sensitive adhesives, a release liner (e.g., a silicone treated paper, or polyolefin) may be releasably bonded to the adhesive to prevent premature adhesion. In use, the flexible structured substrate may be adhered to a rigid substrate, for example, to facilitate positioning in an analytical device.

Figure 2:
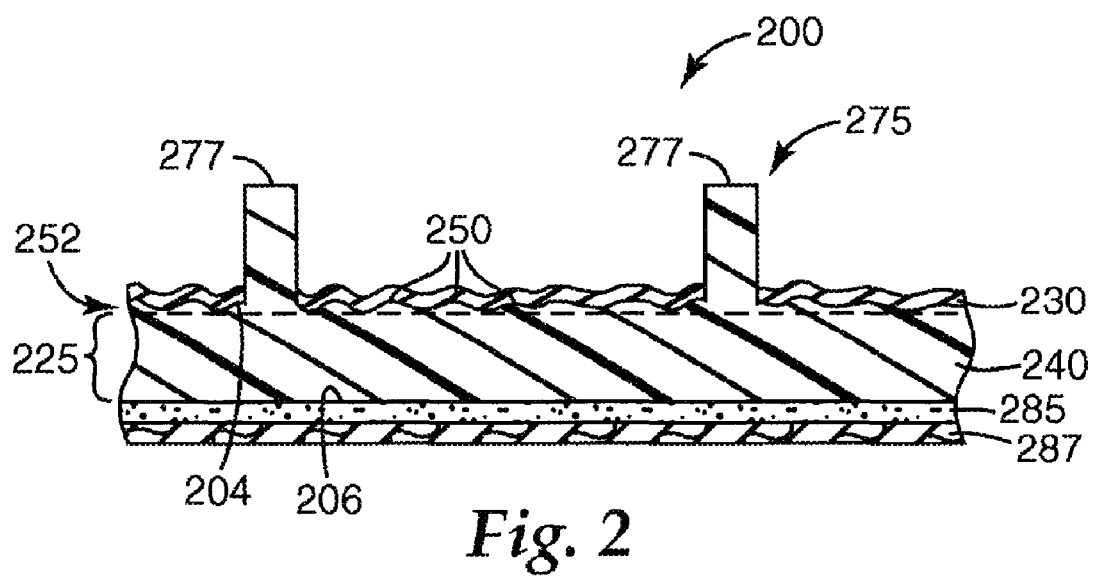
FIG. 2 is a cross-sectional schematic drawing of an exemplary structured substrate according to one embodiment the present invention.

FIG. 2, not drawn to scale, depicts one embodiment of a particularly useful structured substrate for carrying out surface-enhanced analytical methods according to the present invention. Flexible structured substrate 200 comprises monolithic polymeric film 240. Film 240 comprises base 225, which has first and second opposed major surfaces 204, 206, respectively. A portion of first major surface 204 is defined by nanostructure 252 consisting of raised nanofeatures 250. Raised nanofeatures 250 outwardly extend from base 225 and have an average height of at least 5 nanometers and less than 1 micrometer. Another portion of first major surface 204 is defined by patterned microstructure 275, which comprises parallel ribs 277. Metal layer 230 is conformably disposed on at least a portion of the raised nanofeatures 250. Optional adhesive layer 285 is disposed on second major surface 206. Optional release liner 287 is releasably bonded to optional adhesive layer 285. In this embodiment, the average height of the nanostructure is in a range of from at least 100 and less than 200 nanometers. Raised nanofeatures 250 are at least partially encompassed within, or overlap, the patterned microstructure 275.

Flexible structured substrates suitable for practicing various aspects of the present invention may be obtained by providing a monolithic polymeric film having nanostructure and optionally a patterned microstructure as described hereinabove. The monolithic polymeric film may be made by any suitable method including, for example, casting a polymeric film (e.g., of molten thermoplastic polymer, or a thermosettable polymer) onto an appropriately textured tool, by embossing a polymeric film using an appropriately textured tool, or by an appropriate etching technique (e.g., laser etching). Casting and embossing may be readily carried out in continuous mode using an appropriately textured tool (e.g., a roll, sleeve, or belt). Examples of casting techniques may be found in, for example, U.S. Pat. No. 4,781,952 (Coscia et al.); U.S. Pat. No. 3,927,692 (Wenrich); U.S. Pat. No. 6,823,653 B1 (Stark et al.); U.S. Pat. No. 6,489,377 B1 (Bicer et al.); U.S. Pat. No. 6,368,534 B1 (Nakamura et al.); the disclosures of which are incorporated herein by reference.

Examples of embossing techniques may be found in, for example, U.S. Pat. No. 5,930,040 (Janovec et al.); U.S. Pat. No. 6,877,216 B2 (Fukuda et al.); U.S. Pat. No. 6,514,597 B1 (Strobel et al.); U.S. Pat. No. 6,527,991 B1 (Bakker et al.); and U.S. Publ. Pat. Appln. No. 2002/0084553 A1 (Nun et al.); the disclosures of which are incorporated herein by reference.

Tools that are useful for casting and/or embossing as described above can be prepared by any suitable method, for example, as is known in the art. In one suitable method, a smooth polished metal roll, belt, sleeve, or plate is provided with a surface continuously covered with nanostructure by a surface modification technique. Suitable techniques include sand blasting; anodic oxidation; chemical vapor deposition; electrodeposition; nanolithography; and reactive ion etching. Further details concerning methods of generating nanostructure on the surface of tools may be found in commonly assigned and concurrently filed U.S. patent application Ser. No. 11/181,150, bearing attorney case no 60939US002 (Zhang), the disclosure of which is incorporated herein by reference.

Once nanostructure has been formed on the surface of the tool, the larger patterned microstructure may optionally be superimposed into the tool, for example, by diamond tooling or laser etching. Further details concerning methods of generating patterned microstructure on the surface of tools may be found in U.S. Pat. No. 6,076,248 (Hoopman et al.); U.S. Pat. No. 6,824,378 (King et al.); U.S. Pat. No. 6,576,887 (Whitney et al.); U.S. Pat. No. 5,300,263 (Hoopman et al.); U.S. Pat. No. 5,792,411 (Morris et al.); U.S. Pat. No. 6,190,594 (Gorman et al.); U.S. Pat. No. 6,622,599 B1 (Ben-Menachem et al.); the disclosures of which are incorporated herein by reference.

Once the monolithic film has been formed, the metal layer is deposited on at least a portion of the nanostructure. Suitable methods for depositing metals are well known in the art and include, for example, metal vapor deposition (e.g., using thermal, e-beam, etc. techniques) and electroless metal deposition.

Objects and advantages of this invention are further illustrated by the following non-limiting examples, but the particular materials and amounts thereof recited in these examples, as well as other conditions and, details, should not be construed to unduly limit this invention.

EXAMPLES

Unless otherwise noted, all parts, percentages, ratios, etc. in the examples and the rest of the specification are by weight, and all reagents used in the examples were obtained, or are available, from general chemical suppliers such as, for example, Sigma-Aldrich Company, Saint Louis, Mo., or may be synthesized by conventional methods.

Preparation of Embossing Tool A

A copper-plated steel roll, diameter of 15.2 centimeters and face length of 25.4 centimeters, was precision machined to get a smooth surface with a roughness $R_a$ of less than 100 nm. The roll was sprayed with Petroleum Naphtha (obtained from Brenntag Great Lakes Company, St. Paul, Minn.) for one minute, followed by spraying with acetone for one minute. The plate was rinsed with water and then sprayed with isopropanol. After the surface was blown dry with compressed air, the roll was plated in a bath composed of: 50 grams/liter of copper sulfate, 80 grams/liter of sulfuric acid, and 2 grams/liter of polyethylene oxide. A current of 54 amperes was applied for 0.5 minutes at 19° C. and the roll was rotated at a rate of 7 revolutions per minute (rpm). The roll was rinsed with deionized water and dried by compressed air. A uniform surface structure was formed. After this structure was obtained, the roll was machined by a diamond tool to cut channels on the surface with the following size: top width of the channel was 55 micrometers, bottom width 23 micrometers wide, and height 170 micrometers. The pitch of the channel was 214 micrometers.

The roll was then sprayed with Petroleum Naphtha obtained from Brenntag Great Lakes Company, St. Paul, Minn., for one minute, followed by spraying with acetone for one minute. The plate was rinsed with water and then sprayed with isopropanol. After the surface was blown dry with compressed air, the roll was dipped into a cleaning tank, which was composed of 60 grams/liter of a metal cleaner obtained under the trade designation "METAL CLEANER 373" from Atotech USA, Inc., Rock Hill, S.C. The solution temperature was 65.6° C. Anodic cleaning was conducted with a current of 23.5 amperes for 1 minute. The roll was taken out of the tank and rinsed with deionized water, followed by spraying with 2% sulfuric acid. The roll was rinse with deionized water again and put into an electroless nickel bath. The bath was composed of electroless nickel plating solutions obtained under the trade designations "AUTONIC MXPA" (100 milliliter/liter), and "AUTONIC LNS" (50 milliliter/liter), both from Stapleton Technologies, Long Beach, Calif. The temperature of the bath was 87° C. The roll was used as the cathode while a current of 15.6 amperes was applied for 20 seconds. The resultant nickel-plated roll was then rinsed by deionized water and dried with compressed air.

Preparation of Structured Polymeric Film A

Figure 3:
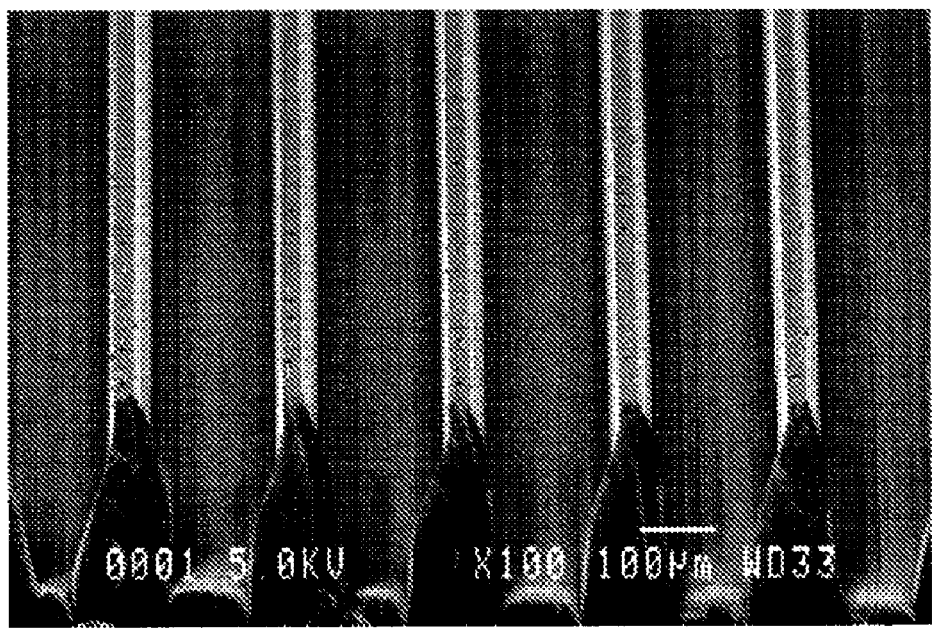
FIG. 3 is a scanning electron micrograph of Structured Polymeric Film A prepared in the Examples.
Figure 4:
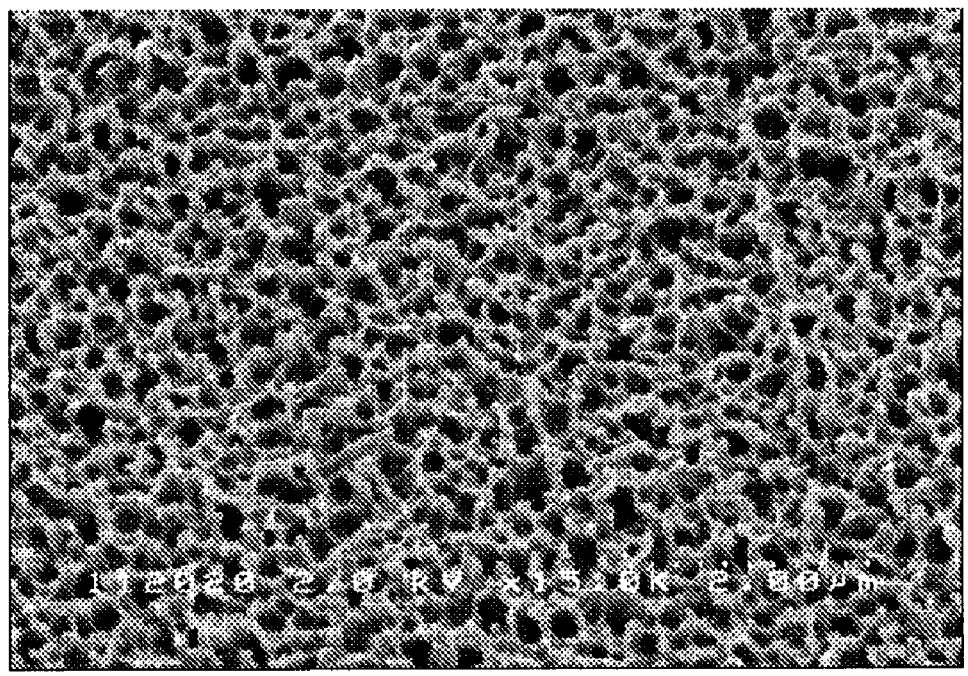
FIG. 4 is a scanning electron micrograph of Structured Polymeric Film A taken between adjacent ribs.

Embossing Roll A was installed, together with a stainless steel nip roll, on a RCP 1.0 extruder made by Randcastle Extrusion System, Inc., Cedar Grove, N.J. and equipped with a flexible lip die. The temperature of the three adjustable heating zones of the extruder were set at 232° C. and the extrusion die temperature was set at 243° C. The rotation rate of the roll was 7 rpm. The top cooling flow rate was set at 10 to 20 gallons per minute (gpm, 38 to 76 liters/minute) and lower cooling flow rate at about 25 gpm (95 liters/minute). Polypropylene, obtained under the trade designation "POLYPROPYLENE 3155" from Exxon Chemical, Houston, Tex. was extruded onto the roll to generate a structured polymeric film. Photomicrographs of surface structures of the structured polymeric film are shown in FIGS. 3 and 4. FIG. 4 is a higher magnification view of the surface between adjacent ribs visible in FIG. 3.

Example 1

Figure 5:
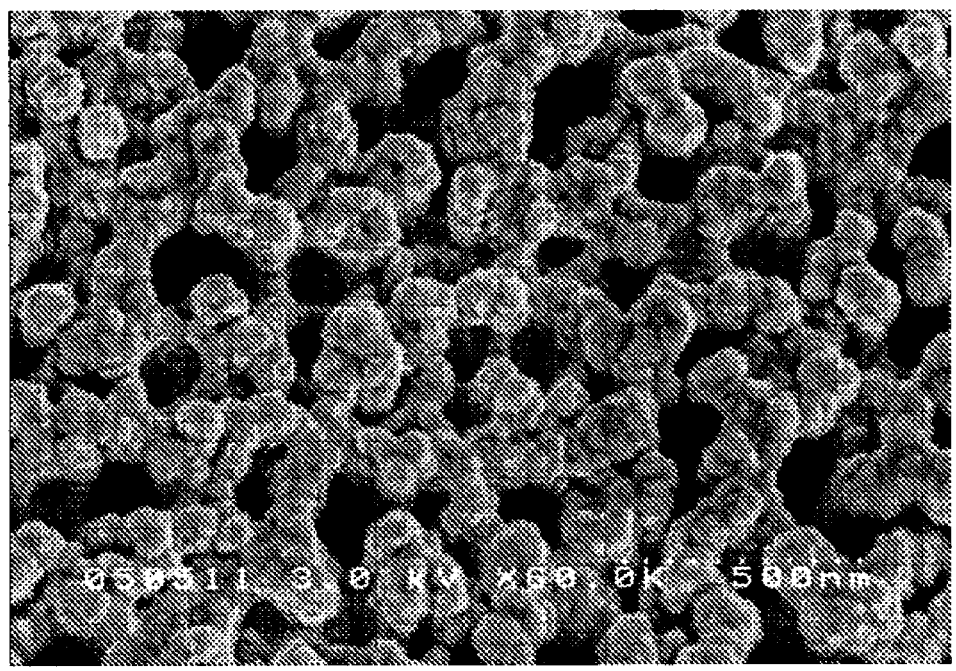
FIG. 5 is a scanning electron micrograph of a gold-coated structured polymeric film prepared in Example 1, taken between adjacent ribs.

A layer of gold, 100 nm thick, was vapor deposited onto the structured surface of Structured Polymeric Film A using a high vacuum deposition system obtained under the trade designation "Mark 50" from CHA Industries, Fremont, Calif. using a base pressure of approximately $10^{-6}$ ton (0.1 mPa). The system used an electron beam system to evaporate the metal, and the gold was deposited at a rate of 10-30 nm/minute. FIG. 5 shows the surface structure of the gold-coated film taken between adjacent ribs (corresponding to FIG. 4) of the resultant gold-coated structured polymeric film.

Preparation of Structured Polymeric Film B

A mandrel having a nickel layer thereon was prepared by chemical vapor deposition using $Ni(CO)_4$ as disclosed in the first paragraph of Example 1 and in FIGS. 1 and 2 of U.S. Pat. No. 6,641,767 B2 (Zhang et al), which disclosure is incorporated herein by reference. The deposited nickel was then separated from the mandrel.

A 9 inch×19 inches (22.9 cm×48.3 cm) piece was cut from the above nickel deposit and mounted on a stainless steel disk having a diameter of 81.3 cm. The resultant composite disk was then dipped into a nickel electroforming bath. The bath composition was as follows: nickel sulfamate (480 g/L), boric acid (35 g/L), wetting agent (10 mL/L, obtained under the trade designation "SNAP L" from MacDermid, Inc., Waterbury, Conn. Electroforming conditions were pH=4.0, temperature of 130° F. (° C.), and current density of 20 amperes/foot² (220 amperes/meter²). The electroforming was conducted for 20 hours to get a 0.5 mm thick nickel deposit. Then, the electroformed nickel was separated from the original nickel deposit sample. The resultant nickel replica was used then as a tool for molding polypropylene.

Polypropylene, obtained under the trade designation "POLYPROPYLENE 3155" from Exxon Chemical, Houston, Tex., was pressure molded between a mirror-polished chrome-plated steel plate and the nickel replica using a heated press obtained under the trade designation "Wabash Compression Molding Machine, Model V75H-24-CLX, from Wabash MPI, Wabash, Ind. The conditions were: pressure=222 pounds/inch² (1.53 MPa), temperature=180° C., time 10 minutes. The pressed polypropylene specimen was separated from the nickel replica after it had cooled to a temperature of about 50° C.

Comparative Metal-Coated Film A

This was Structured Polymeric Film B on which a 50 nm thickness layer of gold had been deposited on the backside (i.e., opposite the nanostructured side) generally as described in Example 1, Example 2

The structured surfaces of Structured Polymeric Films A-B were vapor coated with a 50 nm layer of gold generally as described in Example 1, resulting in Gold-coated Structured Polymeric Films A-B, respectively.

Gold-coated Structured Polymeric Films A-B and Comparative Metal-Coated Film A were each spin-coated with 0.25 milliliter of a 4-millimolar solution of bipyridine onto the metal layer.

A 780-nanometer wavelength diode laser (obtained the trade designation "Renishaw 780/50" from Renishaw, PLC, New Mills, Wotton-under-Edge, Gloucestershire, United Kingdom) was sent through a micro-Raman system (obtained the trade designation "Renishaw M-1000" from Renishaw, PLC). The laser beam was sent through optics set to 500×, and the intensity of the beam was estimated to be no more than 25 milliwatts (1.5 joules/second) at the surface. Collection time was 1 second.

Figure 6:
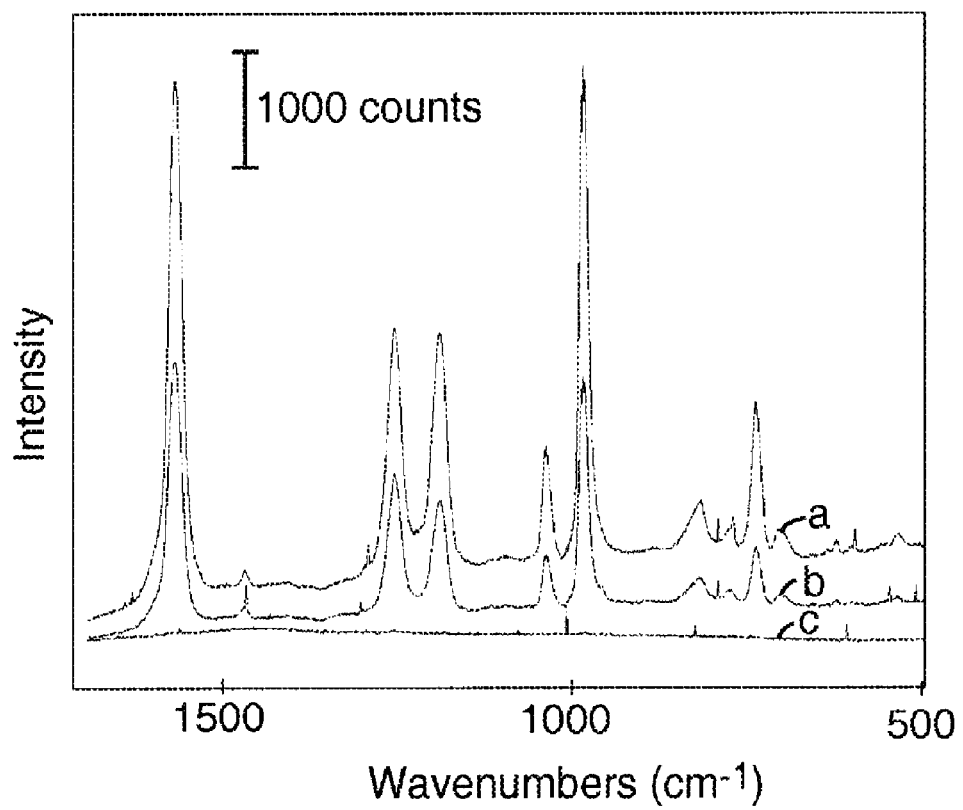
FIG. 6 is a graphical representation of Raman Spectra of bipyridine obtained in Example 2.

Raman spectra of bipyridine obtained from these films is shown in FIG. 6, wherein: curve c) corresponds to Comparative Metal-Coated Film A; curve b) corresponds to Gold-coated Structured Polymeric Film B; and curve a) corresponds to Gold-coated Structured Polymeric Film A.

Example 3

Surface enhanced Raman spectra were obtained for the adsorbed molecule bipyridine on Structured Polymeric Films A-B wherein the structured surface of the film had been vapor coated with various thicknesses of gold generally as described in Example 1. The SERS peak area for the 1600 $cm^{-1}$ bipyridine peak for the two different surfaces was obtained. Table 1 (below) reports the measured variation in SERS peak area with gold thickness.

TABLE 1

| Gold thickness, nanometers | Structured Polymeric Film | Peak area, counts/second |
| --- | --- | --- |
| 50 | A | 125000 |
| 100 | A | 311000 |
| 200 | A | 158000 |
| 50 | B | 61300 |
| 100 | B | 53700 |
| 200 | B | 128000 |

Various modifications and alterations of this invention may be made by those skilled in the art without departing from the scope and spirit of this invention, and it should be understood that this invention is not to be unduly limited to the illustrative embodiments set forth herein.

What is claimed is:

1. A structured substrate comprising:
   (a) a monolithic polymeric film comprising:
      a base having first and second opposed major surfaces, wherein at least a portion of the first major surface is at least partially defined by:
      a patterned microstructure outwardly extending from the base; and
      nanostructure having an average height of at least 100 and less than 200 nanometers, wherein the nanostructure is at least partially encompassed within, or overlaps, the patterned microstructure,
         wherein the nanostructure consists of discrete nanofeatures at an areal density of at least about $1 \times 10^8$ nanofeatures/cm$^2$ and wherein the projected area of the nanostructure onto the base of the film is at least 50% more than the corresponding surface area of the base; and
   (b) a metal layer conformably disposed on at least a portion of the nanostructure, wherein the structured substrate is flexible.

2. A structured substrate according to claim 1, wherein the structured substrate has the form of a tape.

3. A structured substrate according to claim 1, wherein the structured substrate comprises a layer of adhesive on the second major surface and a release liner releasably adhered to the adhesive layer.

4. A structured substrate according to claim 1, wherein the microstructure is regular.

5. A structured substrate according to claim 1, wherein the average thickness of the metal layer is in a range of from 5 nanometers to 50 nanometers, inclusive.

6. A structured substrate according to claim 1, wherein the height of the microstructure is at least 10 micrometers.

7. A structured substrate according to claim 1, wherein at least one region of the microstructure encompasses at least a portion of the nanostructure, and wherein the at least one region has an average width of at least 1 micrometer.

8. A structured substrate according to claim 1, wherein the microstructure comprises at least one of ribs or posts.

9. A structured substrate according to claim 1, wherein the metal is selected from the group consisting of silver, gold, copper, and platinum.

10. A structured substrate according to claim 1, wherein the substrate is in roll form.

11. A structured substrate according to claim 1, further comprising a reagent bound to at least a portion of the metal layer.

12. A method of manufacturing a structured substrate comprising:
   providing a tool having a continuous surface with a first patterned microstructure thereon with the continuous surface of the tool also having thereon a first nanostructure comprised of discrete nodules wherein at least 80 percent of the nodules have a maximum width in a range of from 100 nanometers to 1 micrometer, and wherein the first nanostructure is essentially free of platelet structures;
   continuously forming a monolithic polymeric film comprising a base having first and second opposed major surfaces, wherein at least a portion of the first major surface comprises a second microstructure having a first height and outwardly extending from the base, wherein the second microstructure is substantially complementary to the first microstructure; and
   the formed monolithic polymeric film further comprising second nanostructure having an average height of at least 100 and less than 200 nanometers, and wherein the second nanostructure is at least partially encompassed within, or overlaps, the microstructure; and
   conformably disposing a metal layer on at least a portion of the nanostructure, wherein the structured substrate is flexible.

13. A method according to claim 12, further comprising:
   disposing a reagent on at least a portion of the metal layer.

14. A method according to claim 12, wherein forming the second microstructure comprises embossing the polymeric film.

15. A method according to claim 12, wherein forming the second nanostructure comprises embossing the polymeric film.

16. A method according to claim 12, further comprising coating an adhesive on the second major surface.

17. A method according to claim 12, wherein the tool is selected from the group consisting of a roll, a belt, and a sleeve.

* * * * *